United States Patent [19]
Suga

[11] Patent Number: 5,579,777
[45] Date of Patent: *Dec. 3, 1996

[54] EXERCISE LEVEL OF DIFFICULTY DATA OUTPUT APPARATUS

[75] Inventor: Fusao Suga, Akishima, Japan

[73] Assignee: Casio Computer Co., Ltd., Tokyo, Japan

[*] Notice: The portion of the term of this patent subsequent to Feb. 9, 2013, has been disclaimed.

[21] Appl. No.: 451,574

[22] Filed: May 26, 1995

Related U.S. Application Data

[63] Continuation of Ser. No. 15,636, Feb. 9, 1993, Pat. No. 5,474,077.

[30] Foreign Application Priority Data

Feb. 18, 1992 [JP] Japan ..................................... 4-30730

[51] Int. Cl.⁶ ..................................................... A61B 5/02
[52] U.S. Cl. ................................ 128/687; 128/690; 422/8
[58] Field of Search ........................ 364/413.01, 413.02, 364/413.04; 128/633, 687, 689, 690, 691; 482/3, 8, 7, 9, 51, 52, 54, 74, 900, 901

[56] References Cited

U.S. PATENT DOCUMENTS

| | | | |
|---|---|---|---|
| 4,164,937 | 8/1979 | Spencer | 128/689 X |
| 4,301,808 | 11/1981 | Taus | 128/689 X |
| 4,367,752 | 1/1983 | Jimenez et al. | 128/689 |
| 4,408,183 | 10/1983 | Wills | 482/3 X |
| 4,566,461 | 1/1986 | Lubell et al. | 482/8 X |
| 4,807,639 | 4/1989 | Shimizu et al. | |
| 4,911,427 | 3/1990 | Matsumoto et al. | 482/3 X |
| 5,018,726 | 5/1991 | Yorioku | 482/9 |
| 5,067,710 | 11/1991 | Watterson et al. | 482/9 |
| 5,186,695 | 2/1993 | Mangseth et al. | 482/51 |
| 5,308,300 | 5/1994 | Chino et al. | 482/52 |
| 5,474,077 | 12/1995 | Suga | 128/687 |

FOREIGN PATENT DOCUMENTS 2052050  1/1981  United Kingdom .................. 128/689

*Primary Examiner*—Angela D. Sykes
*Assistant Examiner*—Samuel G. Gilbert
*Attorney, Agent, or Firm*—Frishauf, Holtz, Goodman, Langer & Chick

[57] ABSTRACT

An exercise level of difficulty data output apparatus outputs exercise level of difficulty of an exercise which a user takes, as exercise level of difficulty data, which can be used for general purposes in the exercise physiology. Using the apparatus, the user can objectively learn the exercise level of difficulty of his (or her) exercise for keeping himself healthy or for developing his physical strength. The exercise level of difficulty data output apparatus calculates exercise level of difficulty data from counted pulse number of the user and his age, and outputs the exercise level of difficulty data. Further, the exercise level of difficulty data output apparatus calculates and displays a predetermined pulse-number range indicating the most suitable exercise level of difficulty for the age of the user.

16 Claims, 14 Drawing Sheets

*U A O*

EXERCISE LEVEL OF DIFFICULTY DATA OUTPUT APPARATUS

This is a continuation of application Ser. No. 08/015,636 filed Feb. 9, 1993 now U.S. Pat. No. 5,474,077.

BACKGROUND OF THE INVENTION

1. Field of the Invention

The present invention relates to an exercise level of difficulty data output apparatus which counts the number of pulses of a user and outputs data representative of exercise level of difficulty based on the counted number of pulses.

2. Description of the Related Art

In general, it is well known that physical exercise increases the number of pulses of an exerciser in proportion to the physical exercise level of difficulty attained by him (or her). Comparison of the number of pulses of the exerciser which is counted immediately after the exerciser has finished exercise with the number of pulses of the exerciser which was counted just before the exerciser started the exercise will indicate exercise level of difficulty attained by the exerciser. Such technique is disclosed in U.S. Pat. No. 4,807,639.

The above conventional technique, however, has problems such that the number of pulses of an exerciser does not indicate whether exercise level of difficulty attained by the exerciser is enough or appropriate for maintaining him (or her) healthy, whether the exercise level of difficulty is satisfactory not only to keep his physical strength but also to develop his physical strength or whether or not an excessive exercise level of difficulty has been attained by the exerciser.

SUMMARY OF THE INVENTION

The present invention has been made to overcome the above conventional problems, and has an object to provide an exercise level of difficulty data output apparatus that is capable of outputting exercise level of difficulty data which can be used for general purposes of exercise physiology.

Another object of the present invention is to provide an exercise level of difficulty data output apparatus which is capable of objectively indicating exercise level of difficulty achieved by an exerciser, and which can be conveniently used by the exerciser for the purpose of maintaining him (or her) healthy or developing his physical strength.

To achieve these objects of the present invention, there is provided an exercise level of difficulty data output apparatus which comprises:

age-data output means for outputting age data;

pulse-number counting means for counting pulses of a user to obtain pulse-number data;

exercise level of difficulty calculating means for calculating exercise level of difficulty data from the pulse-number data obtained by said pulse-number counting means and the age data output by said age-data output means; and output means for outputting the exercise level of difficulty data calculated by said exercise level of difficulty calculating means.

The above output means is transmitting/outputting means which externally supplies the exercise level of difficulty data calculated by the exercise level of difficulty calculating means. That is, the output means includes displaying/outputting means such as a liquid crystal display device for visually displaying the exercise level of difficulty data and printing/outputting means for printing the exercise level of difficulty data to make a hard copy.

With the above structure of the exercise level of difficulty data output apparatus, exercise level of difficulty data is calculated from the pulse-number data representative of the counted number of pulses of the user and the age data, and the calculated exercise level of difficulty data is output. The exercise level of difficulty data thus obtained therefore is output as data that may be used for general purposes of the exercise physiology. Further, the exercise level of difficulty may objectively be measured by the exercise level of difficulty data output apparatus of the invention and may be used for maintaining the user healthy and/or for developing physical strength of the user.

DETAILED DESCRIPTION OF THE PREFERRED EMBODIMENTS

First Embodiment

Now, the first embodiment of the present invention will be described in detail with reference to the accompanying drawings.

In the first embodiment, the present invention is applied to an electronic wrist watch.

Figure 1:
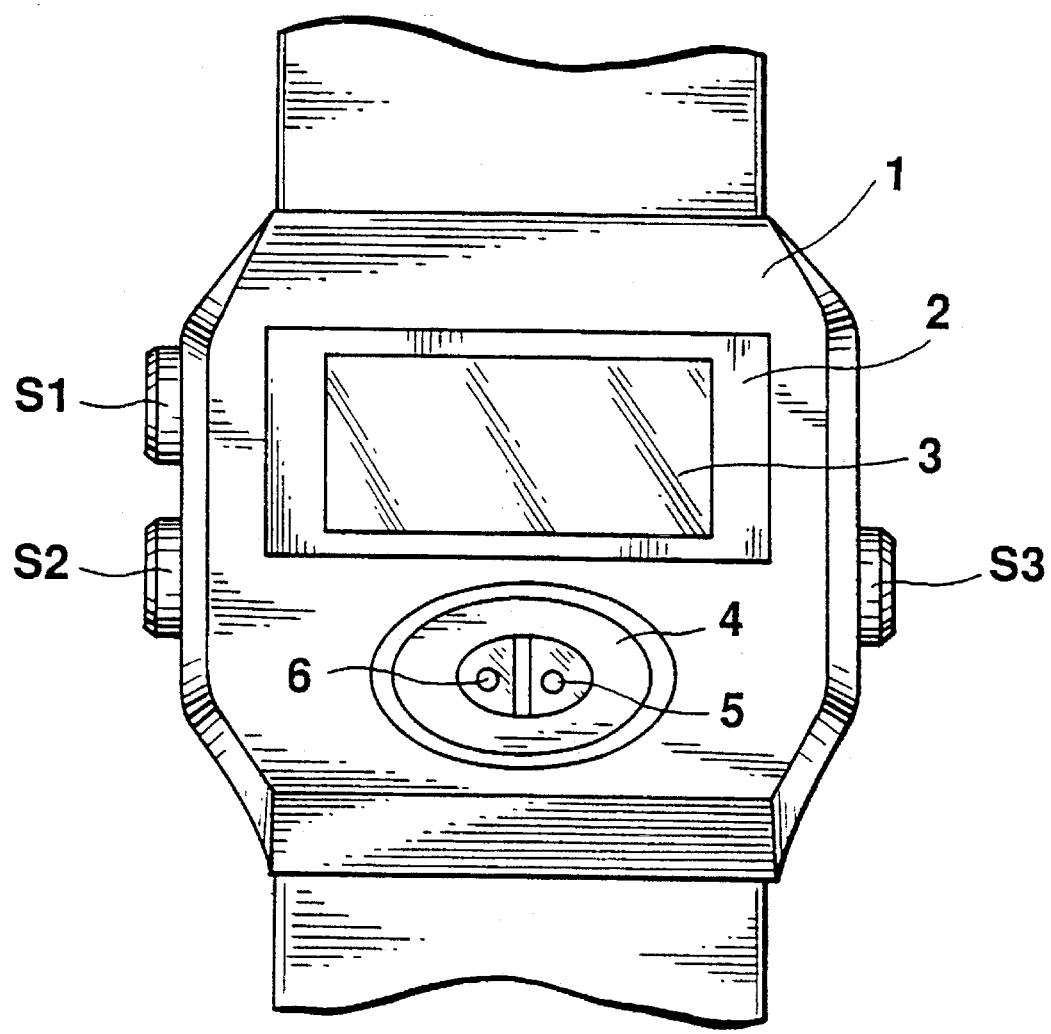
FIG. 1 is a front view showing an external view of a first embodiment of an electronic watch according to the present invention.

FIG. 1 is a front view showing an external view of the electronic wrist watch to which the present invention is applied. In FIG. 1, a reference numeral 1 stands for a casing of the electronic wrist watch, a reference numeral 2 stands for a watch glass, a reference numeral 3 designates a liquid crystal display device and a reference numeral 4 is a pulse detecting unit. The pulse detecting unit 4 optically senses a blood flow in a fingertip of a user, detecting the density of hemoglobin in blood, thereby detecting pulses. The pulse detecting unit 4 comprises a light emitting element (for example, a light emitting diode) 5 and a light receiving element (for example, a photo transistor) 6. The number of pulses is counted with the fingertip of the user being in contact with the pulse detecting unit 4. On a side wall of the watch casing 1 are arranged keys of a push button type S1–S3.

Figure 2:
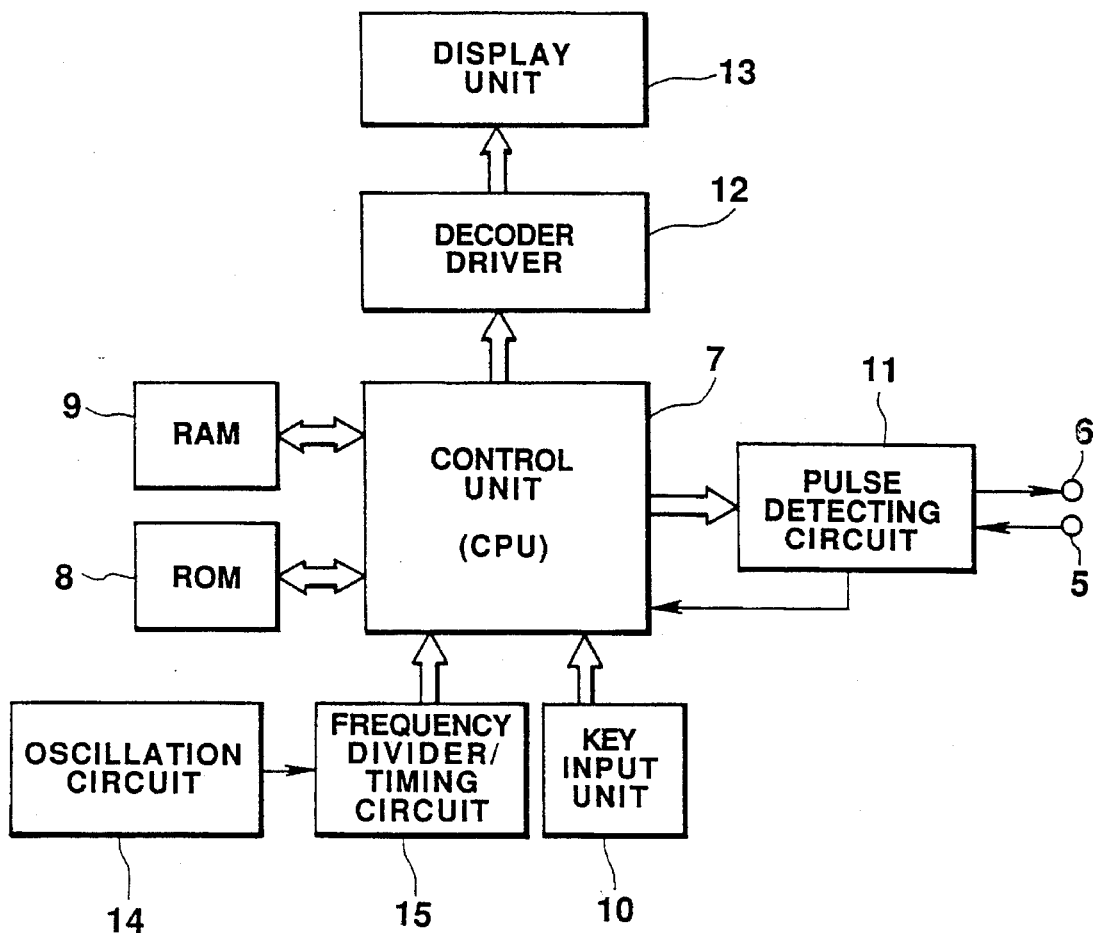
FIG. 2 is a circuit diagram of the electronic watch.

FIG. 2 is the circuit diagram of the electronic watch. A control unit (CPU) 7 installed within the electronic wrist watch is a central processing unit which controls various units in accordance with a micro-program previously stored in a ROM 8, and performs various processes such as a time counting process, a pulse-number counting process and a calculating process of exercise level of difficulty. A RAM 9 is a memory for storing various data, which will be described in detail later. A key input unit 10 is provided with the keys S1–S3 shown in FIG. 1, and outputs a key input signal in response to an actuation of the key. The key S1 is operated to renew a content of a mode register M, thereby an operation mode is changed. The key S2 is for inverting a content of a flag register F. The key S3 is for allowing other processes to be performed.

A pulse detecting circuit 11 is connected with the light emitting element 5 and the light receiving element 6, which are included in the pulse detecting unit 4 shown in FIG. 1. The pulse detecting circuit 11 senses decreases in the intensity of light received by the light receiving element 6 from the light emitting element 5, caused by changes of a blood flow, thereby detecting pulses. Further, the pulse detecting circuit 11 outputs to control unit (CPU) 7 a pulse signal which varies in synchronism with the detected pulses. A decoder driver 12 decodes display data supplied from the control unit 7, and supplies a display driving signal to a display unit 13.

The display unit 13 is composed of the liquid crystal display device 3, and is driven by the display driving signal supplied from the decoder driver 12, thereby displaying various data. A detailed structure of the display unit 13 will be described later. An oscillation circuit 14 generates a clock signal of a predetermined frequency, and supplies the clock signal to a frequency divider/timing circuit 15. The frequency divider/timing circuit 15 divides the supplied clock signal to generated various timing signals such as a time counting signal, and supplies these timing signals to the control unit 7.

Figure 3:
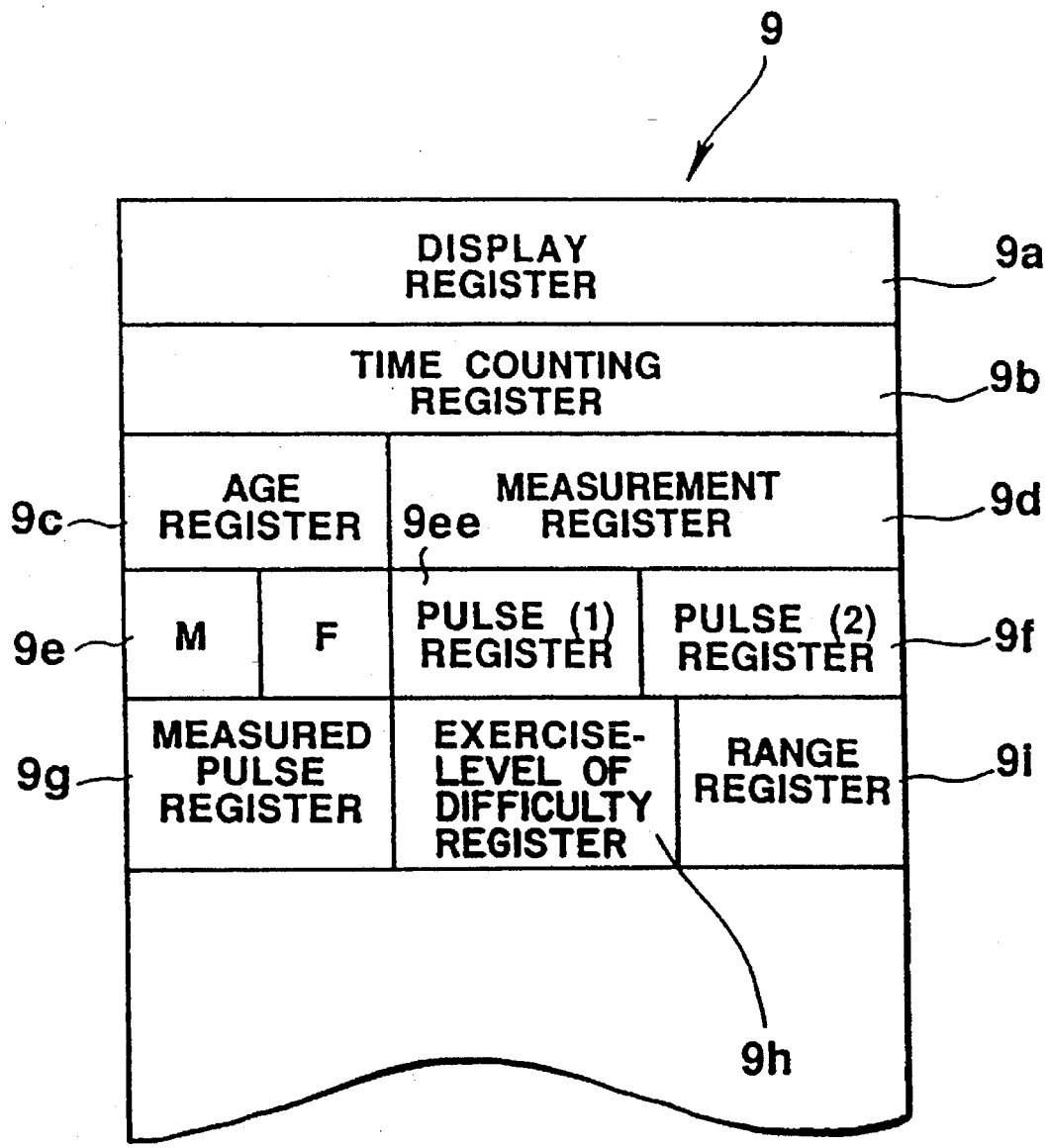
FIG. 3 is a view showing a memory structure of RAM of FIG. 2.

FIG. 3 is a view showing the memory structure of the RAM 9.

A display register 9a in the RAM 9 is a register for storing display data to be displayed on the display unit 13. A time counting register 9b is a register for storing a current time and a current date. An age register 9c is a register which stores age data of a user input from the key input unit 10. A measurement register 9d is a register for storing a time during which the user exercises.

The mode register M is a register which stores mode data. The mode data "M=0" represents a time display mode in which a time is displayed has been set. The mode data "M=1" represents an age setting mode in which an age has been set and the pulse data most suitable for the age is displayed. The mode data "M=2" represents a pulse measuring mode in which a time counting process is performed, a pulse is displayed and exercise level of difficulty is displayed.

The flag register F is a register which stores a flag representative of a time measuring state while the user is exercising. The flag "F=1" represents that a time counting process is being effected. A pulse (1) register 9e is a register which stores pulse-number data corresponding to 60% (the lower limit of the most suitable pulse-number data) of the maximum pulse number. A pulse (2) register 9f is a register which stores pulse data corresponding to 80% (the upper limit of the most suitable pulse-number data) of the maximum pulse number. A measured pulse register 9g is a register which stores measured pulse-number data. An exercise level of difficulty register 9h is a register for storing exercise level of difficulty data which represents a ratio (%) of a measured pulse number to the maximum pulse number. The exercise level of difficulty data is expressed in percent.

A range register 9i is a register which stores range data which indicates whether or not a measured pulse number falls within a range of 60% to 80% of the maximum pulse number. Hereafter, a pulse number which falls within the range of 60% to 80% of the maximum pulse number is referred to as the most suitable pulse number. The range data takes three values: "0", "1" and "2". The range data "0" represents that a measured pulse number is the most suitable pulse number or the measured pulse number falls within the above mentioned range. The range data "1" represents that the measured pulse number is lower than the most suitable pulse number. The range data "2" represents that the measured pulse number is higher than the most suitable pulse number.

The operation of the first embodiment of the present invention will be described referring to the flow chart of FIG. 4.

The control unit 7 stays usually in a halt state, waiting for the time counting signal from the frequency divider/timing circuit 15 or for a key input of the key input unit 10 at step A1.

Upon receipt of the time counting signal, the control unit 7 advances from step A1 to step A2 to execute a time counting process. In the time counting process, present time data (including date, day of the week) stored in the time counting register 9b of the RAM 9 is updated. At step A3, the control unit 7 judges whether "M=2" and "F=1" are true. More specifically, the control unit judges whether or not the content of the mode register M is "2" (the pulse measuring mode) and the content of the flag register F is "1" (under time counting process). When "YES" at step A3, the control unit 7 goes to step A4 and when "NO" at step A3, then the control unit 7 goes to step A9.

When "M=0" is true, i.e., when the time display mode has been set, the control unit 7 judges "NO" at step A3 and goes to step A9. In the display mode at step A9, a pertinent indication is displayed. That is, when "M=0" is true, current time data stored in the time counting register 9b is displayed as shown at (A) in FIG. 5. At a first numeral display portion 13a of the display unit 13, current time data: "10: 58 50" (58 minutes and 50 seconds past 10 o'clock) is displayed. At a second numeral display portion 13b, week data: "SU" (Sunday) and date data: "6-30" (June 30) are displayed. Then the control unit 7 returns from step A9 to step A1.

Figure 5:
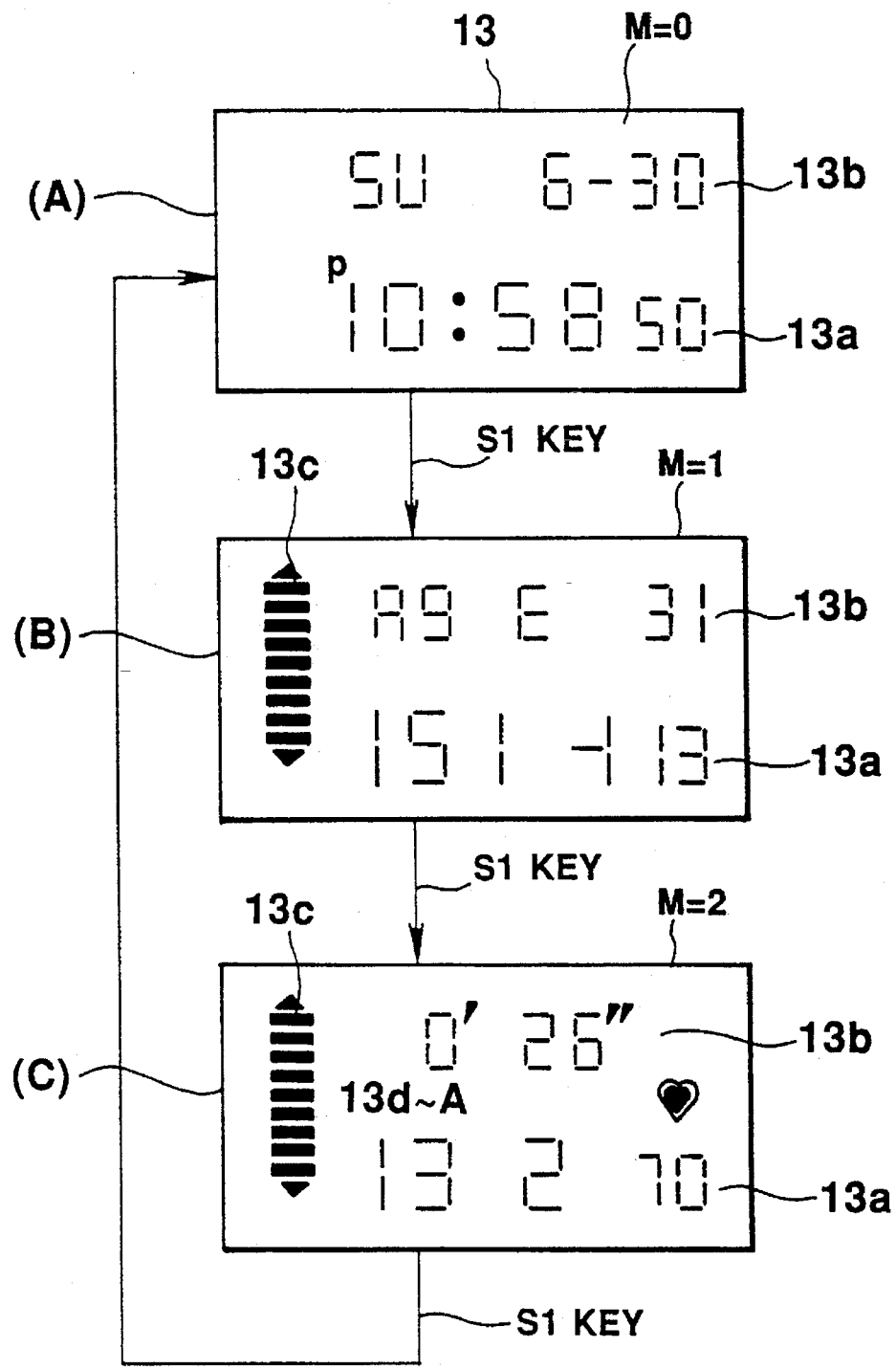
FIG. 5 is a view showing indications in various modes.

When the key S1 is manipulated while the indication shown at (A) of FIG. 5 is displayed on the display unit 13, the operation mode is changed. That is, receiving the key input from the key input unit 10, the control unit 7 advances from step A1 to step A10, where it is judged whether the key S1 is manipulated. When "YES" at step A10, the control unit 7 goes to step A11. When "NO" at step A10, the control unit 7 goes to A12. At step A11, the content of the mode register M is updated, i.e., from "0" to "1", from "1" to "2" or from "2" to "0". When the key S1 is manipulated in the time display mode (M=0), "M=0" is updated to "M=1" (the age setting mode) at step A11. Then, the control unit 7 advances from step A11 to step A9.

At step A9, based on the contents of the pulse (1) register 9e and the pulse (2) register 9f, the lower limit and the upper limit of the most suitable pulse-number data, for example "151–113", are displayed at the first numeral display portion 13a in the age setting mode ("M=1"), as shown at (B) in FIG. 5. At the second numeral display portion 13b is displayed age data, "AGE 31" (the user is 31 years of age) stored in the age register 9c. The range of the most suitable pulse number is displayed at the pulse-number bar-graph display portion 13c. In other words, appropriate number of bars of the pulse-number bar-graph display portion 13c are kept turned on to indicate the most suitable pulse-number range.

Figure 6:
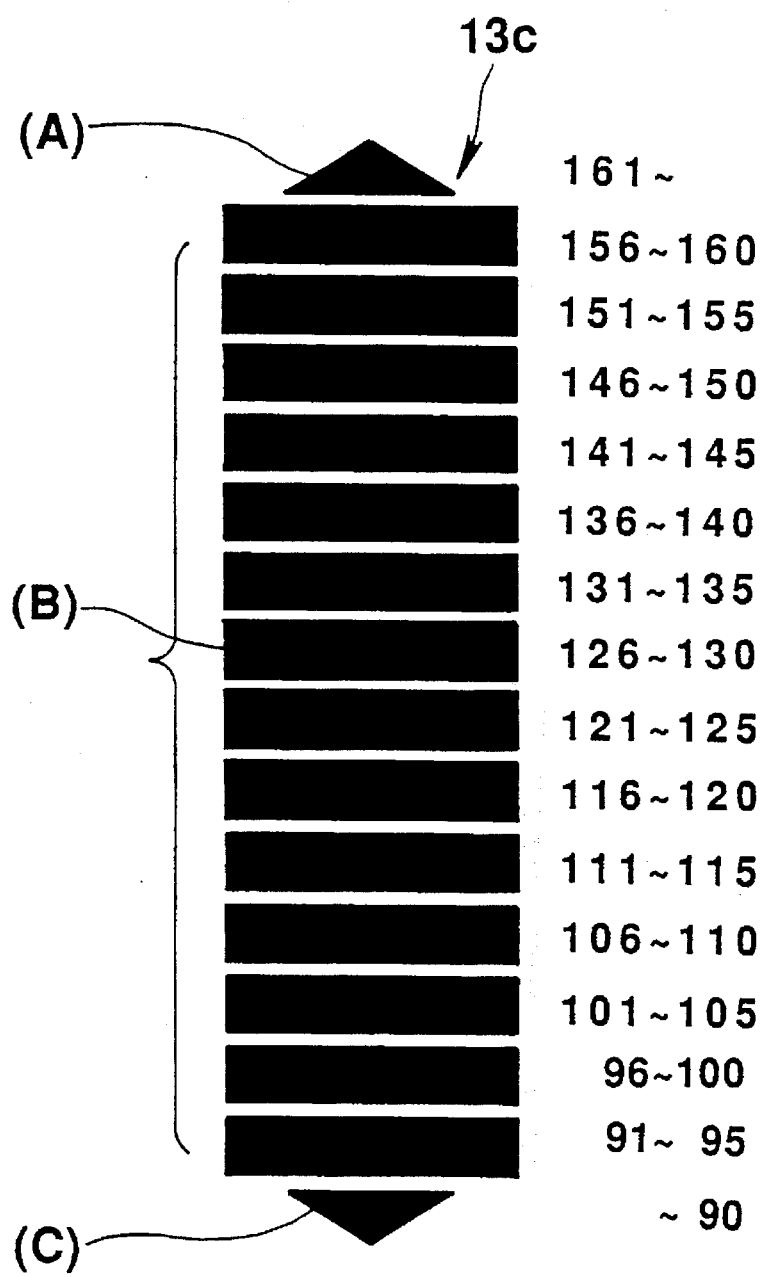
FIG. 6 is a view showing a structure of a pulse-number bar-graph display portion 13c.

FIG. 6 is a view showing a structure of the pulse-number bar-graph display portion 13c.

As shown in FIG. 6, the pulse-number bar-graph display portion 13c is composed of an upper limit indicating segment (A) of a triangle shape, 13 units of segments (B) of a rectangle shape for indicating a pulse-number range and a lower limit indicating segment (C) of a triangle shape. The segment (A) is arranged with the vertex disposed upward as viewed in FIG. 6 while the segment (C) is arranged with the vertex disposed downward. The pulse-number bar-graph display portion 13c schematically indicates a pulse-number range at the most suitable exercise load and a measured pulse number.

The upper limit indicating segment (A) is turned on when a measured pulse number or the pulse-number range at the most suitable exercise load exceeds a pulse number "160". The segments (B) each indicate a pulse number "5" and are provided corresponding to pulse-number ranges such as "91–95", "96–100", ..., "151–155" and "156–160", printed on the display unit 13. The lower limit indicating segment (C) is turned on when a measured pulse number or the pulse-number range at the most suitable exercise load is not more than a pulse number "90".

In the display process at step A9, therefore, 9 units of rectangle-shaped segments (B) of the pulse-number bar-graph display portion 13c, which correspond to pulse numbers from "151" to "113", are steadily turned on as shown at (B) in FIG. 5. Then, the control unit 7 returns from step A9 to step A1.

Update of age data is effected by manipulating the key S2 while the indication shown at (B) of FIG. 5 is displayed on the display unit 13. When the key S2 is manipulated, the control unit 7 advances from step A1 to step A10. The control unit 7 judges "NO" at step A10, and advances to step A12. It is judged at step A12 whether the key S2 is manipulated. When "YES" at step A12, then the control unit 7 goes to step A13 while, when "NO" at step A12, then the control unit goes to step A16.

When it is judged at step A12 that the key S2 has been manipulated, the control unit 7 goes to step A13, where it is judged whether "M=1" is true, i.e., it is judged whether the age setting mode has been set. When "YES" at step A13, then the control unit 7 goes to step A14 while, when "NO" at step A13, then the control unit goes to step A17.

When "M=1" is true, i.e., when the age setting mode has been set, the control unit 7 goes to step A14, where an age updating process is effected. In the age updating process at step A14, "+1" is added to age data stored in the age register 9c, thereby the age data being updated. At the following step A15, a most suitable pulse-number calculating process is effected. In the most suitable pulse-number calculating process at step A15, pulse numbers of 60% and 80% of the maximum pulse number for the user of the age are calculated based on the updated age, and the most suitable pulse-number range for the age is defined by these calculated pulse numbers: the lower limit of the most suitable pulse number and the upper limit of the most suitable pulse number. The pulse numbers of 60% of the maximum pulse number for the user of the age is stored in the pulse (1) register 9ee and the pulse number of 80% of the maximum pulse number is stored in the pulse (2) register 9f. For example, when the age data is "31", the maximum pulse number N-max for the age "31" can be calculated from the following equation: N-max= 220−31, as will be described later. The pulse number "131" of 60% of the maximum pulse number (N-max) "189" is stored as the lower limit of the most suitable pulse number in the pulse (1) register 9e while the pulse number "151" of 80% of the maximum pulse number "189" is stored as the upper limit of the most suitable pulse number in the pulse (2) register 9f. Then, the control unit 7 advances from step A15 to step A9. Similarly, at step A15, the upper limit and the lower limit of the most suitable pulse number and age data are displayed, and further the most suitable pulse-number range is displayed by the pulse-number bar-graph display portion 13c.

When "NO" at step A13, then the control unit 7 goes to step A17. It is judges at step A17 whether "M=2" is true, i.e., whether the pulse measuring mode has been set. When "YES" at step A17, then the control unit 7 goes to step A18 while, when "NO" at step A17, then the control unit 7 goes to step A9. When the pulse measuring mode has been set, i.e., when "M=2" is true, the control unit 7 goes to step A18. At step A18, the content of the flag register F is inverted, thereby "0" being changed to "1" or "1" to "0". In other words, when the key S2 is manipulated in the pulse measuring mode (M=2), the content of the flag register F is inverted. After the process at step A18 has been executed, the control unit 7 goes to step A9.

When the time counting signal is output while "M=2" and "F=1" are true, processes at steps A1 to A3 will be executed. When "YES" at step A3, the control unit goes to step A4. When "M=2" and "F=1" are true, the pulse measuring mode has been set and the time counting process is going on. The time counting process is effected at step A4. More specifically, time counting data stored in the measurement register 9d of RAM 9 is updated and time during which the user is exercising is measured.

At step A5, the pulse measuring process is effected. During the pulse measuring process, when a fingertip of the user is placed on the pulse detecting unit 4, the pulse detecting circuit 11 detects pulses by means of the light emitting element 5 and the light receiving element 6, and outputs the pulse signals to the control unit 7. The control unit 7 measures time intervals between successive pulse signals, i.e., pulse intervals to calculate the number of pulses per minute. Data of the pulse number per minute (pulse-number data) is stored in the measured pulse register 9g of the RAM 9. Since measurement of the number of pulses takes considerable time, it is judged at the following step A6 whether the pulse measurement process has been finished at step A5. When the pulse measurement process has not been finished, the control unit 7 returns through the display process of step A9 to step A1.

The control unit 7 repeatedly executes processes of steps A1 to A5, thereby measuring pulse-number data (pulse number per minute), for example, "132", and stores the pulse-number data in the measured pulse register 9g, and then the control unit 7 returns from step A6 to step A7.

In an exercise level of difficulty calculating process at step A7, exercise level of difficulty is calculated from the measured number of pulses. The exercise level of difficulty is calculated from the measured pulse-number data and age data of a user.

Statistical data of people show as follows:

The upper limit of the maximum pulse number for people of 20 years of age is approximately 200 pulses/minute. The upper limit of the maximum pulse number for people of 40 years of age is approximately 180 pulses/minute. The upper limit of the maximum pulse number for people of 60 years of age is approximately 160 pulses/minute.

From the above data, the maximum pulse number Y for the use of X years of age will be expressed by the following equation: Y=220−X, where X stands for an age of the user.

At the step A7, the control unit 7 calculates exercise level of difficulty, by performing an arithmetic operation: exercise level of difficulty=(measured pulse number)/(220−age)× 100. The exercise level of difficulty calculated from the above equation is stored in the exercise level of difficulty register 9h of the RAM 9. The exercise level of difficulty data stored in the exercise level of difficulty register 9h represents a ratio expressed in percent of the measured pulse number to the maximum pulse number for the user of the age. In other words, the exercise level of difficulty data is data representative of a ratio of exercise level of difficulty of exercise which the user took to the maximum exercise level of difficulty accomplished at the maximum pulse number for an age of the user. In this case, as the age is "31", the maximum pulse number "189" will be obtained as follows: 220−31=189, and, as the measured pulse-number data is "132", the exercise level of difficulty data will be "70"% (132/189×100=70 (%)), which is stored in the exercise level of difficulty register 9h.

At step A8, a range discriminating process is effected. In the range discriminating process at step A8, it is judged whether the measured pulse-number data "132" falls within a range of most suitable exercise load.

In general, it is said that 60% to 80% of the maximum exercise level of difficulty is the most suitable exercise load, and is most suitable exercise level of difficulty for a human body in the exercise physiology. In the range discriminating process, it is judged whether the measured pulse-number data falls within a range defined by 60% of the maximum exercise level of difficulty and 80% of the maximum exercise level of difficulty, which have been stored in the pulse (1) register 9ee and the pulse (2) register 9f, respectively. A result of the discrimination is stored in the range register 9i. In this case, pulse-number data "113" corresponding to 60% of the maximum pulse number was stored in the pulse (1) register 9ee when the age data was updated at step A15, and pulse-number data "151" corresponding to 80% of the maximum pulse number was stored in the pulse (2) register 9f. Therefore, the content of the measured pulse register 9g is compared with those stored in the pulse (1) register 9ee and the pulse (2) register 9f. When the measured pulse-number data is less than the most suitable exercise load, the resultant "1" is stored in the range register. When the measured pulse-number data is within the range of the most suitable exercise load, the resultant "0" is stored in the range register. When the measured pulse-number data is more than the most suitable exercise load, the resultant "2" is stored in the range register. In this case, as the measured pulse-number data is "132", the resultant "0" is stored in the range register.

At step A9, when "M=2" is true, i.e., when the pulse measuring mode has been set, the measured pulse-number data "132" and the exercise level of difficulty data "70"% are displayed at the first numeral display portion 13a, and time counting data "0'26" (0 minute and 26 seconds) is displayed at the second numeral display portion 13b, as shown at (C) in FIG. 5. At the pulse-number bar-graph display portion 13c, 9 units of segments (B) for indicating a pulse-number range, which correspond to pulse numbers from "151" to "113", are steadily turned on to indicate the most suitable pulse-number range "151–113", and a segment (B) for indicating a pulse-number range, which corresponds to a pulse number "131–135", is turned on in a blinking manner at a frequency of 2 Hz.

Figure 7:
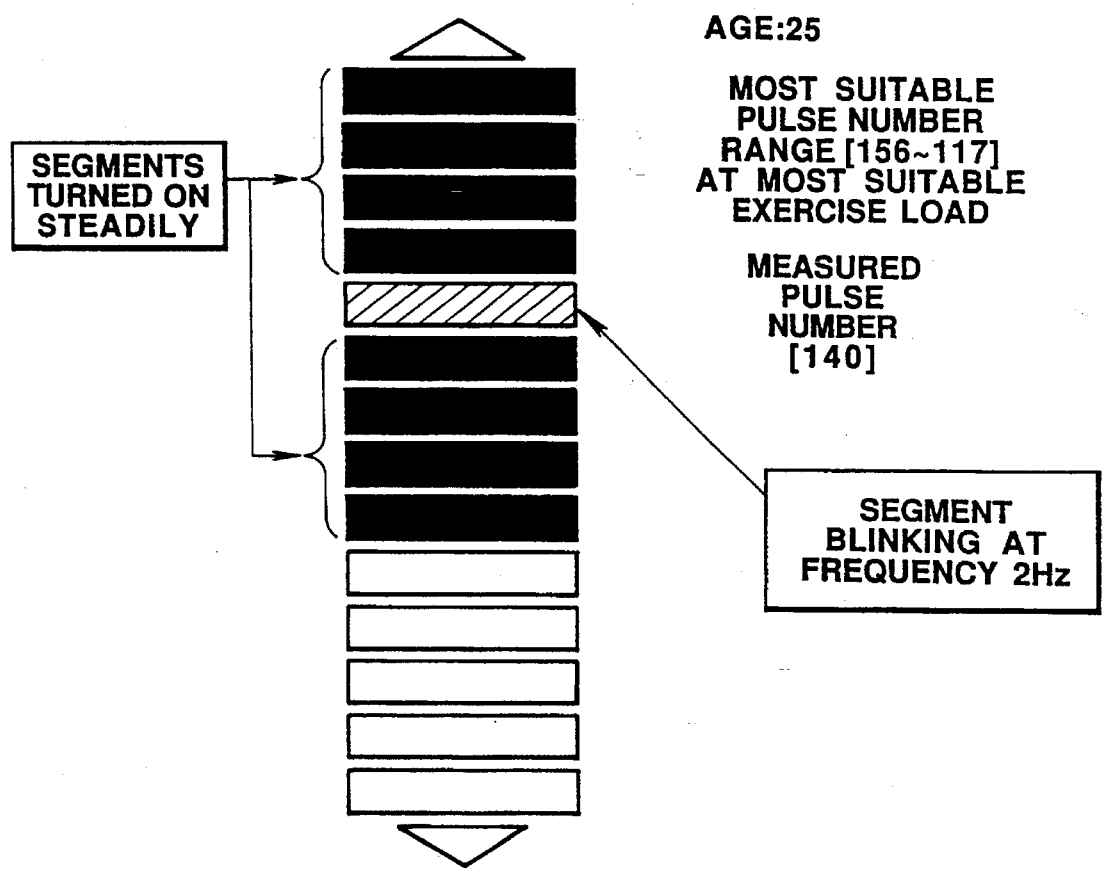
FIG. 7 is a view showing an indication on the pulse-number bar-graph display portion 13c.
Figures 8, 9:
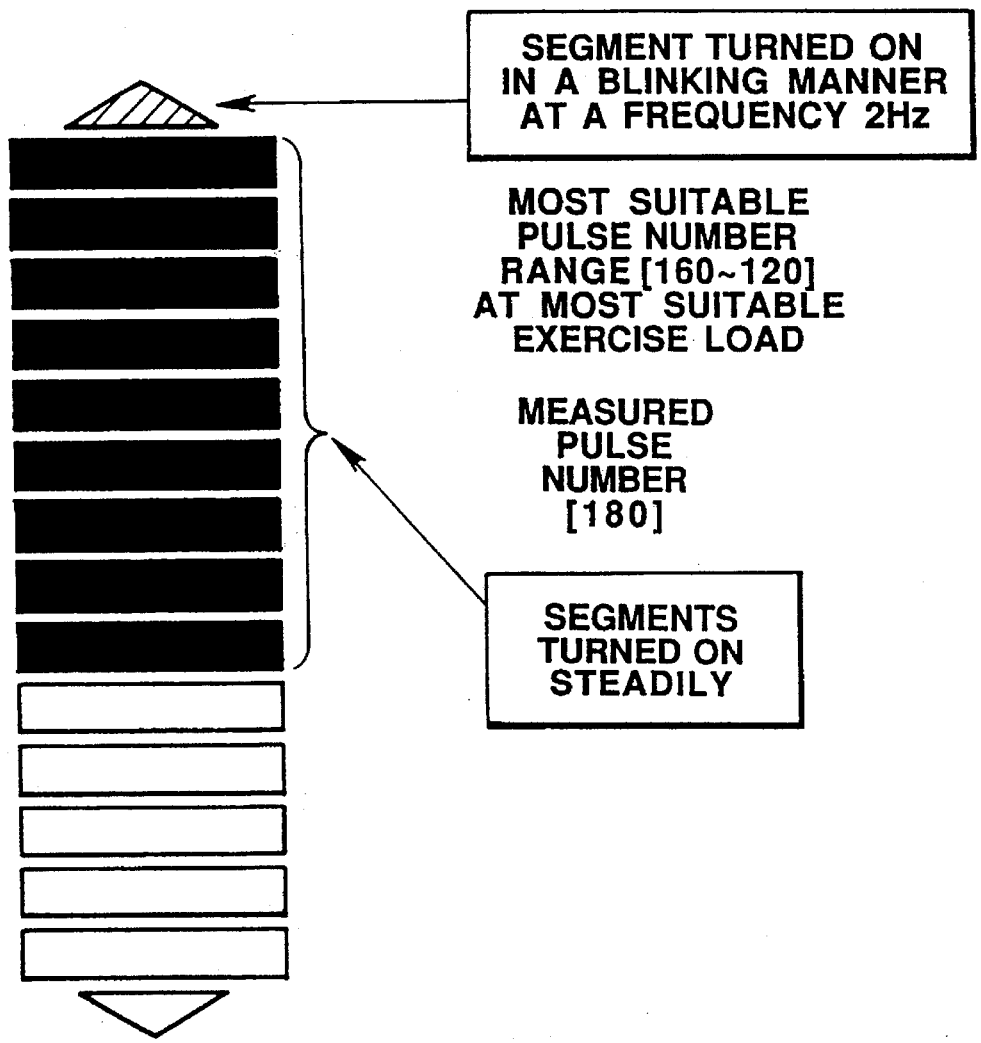
FIG. 8 is a view showing another indication on the pulse-number bar-graph display portion 13c.
FIG. 9 is a view showing a structure of an exercise level of difficulty display portion 13d.

FIGS. 7 and 8 are views showing detailed examples of indications shown at the pulse-number bar-graph display portion 13c.

FIG. 7 is a view of the pulse-number bar-graph display portion 13c which indicates age data "25", the most suitable pulse-number range "156–117" at the most suitable exercise load, and measured pulse-number data "140". 9 units of segments (B) for indicating a pulse-number range, which correspond to pulse numbers from "156" to "117", are steadily turned on to indicate the most suitable pulse-number range "156–117", and a segment (B) for indicating a pulse-number range, which corresponds to a pulse number "136–140", is turned on in a blinking manner at a frequency of 2 Hz.

FIG. 8 is a view of the pulse-number bar-graph display portion 13c which indicates age data "20", the most suitable pulse-number range "160–120" at the most suitable exercise load, and measured pulse-number data "180". As the measured pulse-number data is more than "160", the upper limit indicating segment (A) is turned on in a blinking manner at a frequency of 2 Hz, and the segments (B) for indicating a pulse-number range, which correspond to pulse numbers from "160" to "120", are steadily turned on to indicate the most suitable pulse-number range "160–120".

Returning to (C) of FIG. 5, indicating segments are displayed at the exercise level of difficulty display portion 13d based on the resultant of the judgement stored in the range register 9i. More specifically, as shown in FIG. 9, indicating segments "U", "A" and "O" are disposed in a lateral direction at the exercise level of difficulty display portion 13d. The indicating segment "U" is turned on when measured pulse number is less than the most suitable pulse number at the most suitable exercise load. The indicating segment "A" is turned on when measured pulse number falls within the most suitable pulse-number range at the most suitable exercise load. Further, the indicating segment "O" is turned on when measured pulse number is more than the most suitable pulse number at the most suitable exercise load. In this case, as the resultant of the judgement "O" is stored in the range register 9i, the indicating segment "A" is turned on. Returning to FIG. 4, after the display process at step A9 has been performed, the control unit 7 returns to step A1.

When a key other than S1 and S2 is manipulated, the control unit 7 goes to step A16 through step A12. At step A16, another key process is performed such as setting or correcting a present time, clearing various registers of the RAM 9. After step A16, the control unit 7 goes to step A9.

In the present embodiment, the above mentioned exercise level of difficulty data are displayed for general purposes in the exercise physiology. The user can objectively learn from the displayed exercise level of difficulty data whether exercise taken by him (or her) is one he desired, and the user can effectively use these data for maintaining his health and/or developing his physical body.

Second Embodiment

Now, the second embodiment of the present invention will be described with reference to FIGS. 10 and 11.

In the first embodiment of the invention, age data is set through the key input. The second embodiment, however, is arranged such that birthday data of the user is previously memorized in a birthday memory and the age data is automatically updated when the memorized birthday data coincides with the present-date data. It should be noted that any structure which is not shown in FIGS. 10 and 11 is the same as the first embodiment.

Figure 10:
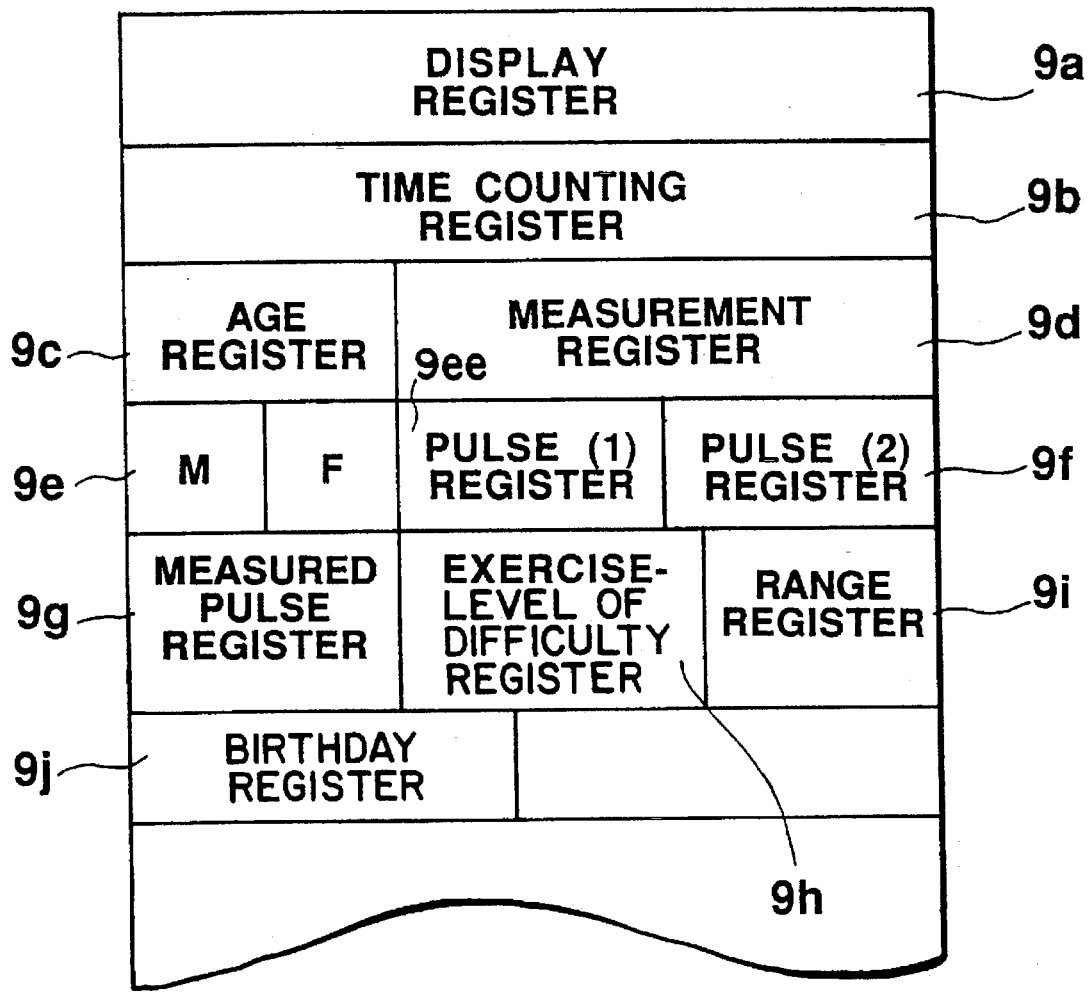
FIG. 10 is a view showing a memory structure of RAM 9 of a second embodiment of the present invention.

FIG. 10 is a view showing a structure of a RAM 9 of the second embodiment of the present invention.

The RAM 9 of the second embodiment includes a birthday memory 9j in addition to the registers of the RAM 9 of the first embodiment. The birthday memory 9j stores date data representative of a birthday of a user. The date data representative of the birthday of the user is hereafter referred to as birthday data.

The birthday data is set in the birthday memory 9j in another key process at step A16. The second embodiment executes four processes shown in a flowchart of FIG. 11 in addition to the processes of FIG. 4. Step A19 to step A22 of FIG. 11 are inserted into the flowchart of FIG. 4 between step A2 and step A3.

An operation of the second embodiment will be described.

Figure 4:
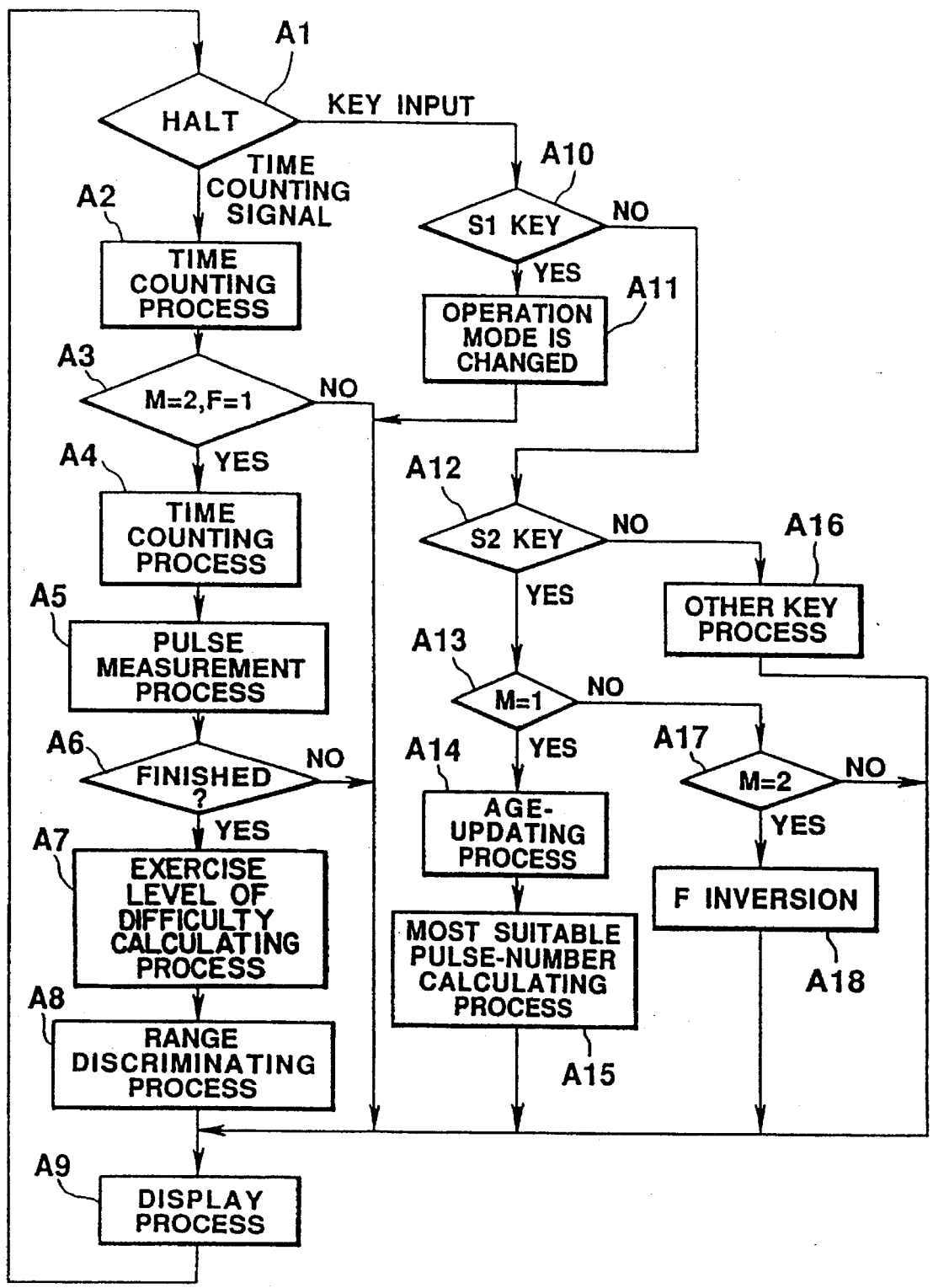
FIG. 4 is a flow chart of operation of the first embodiment.
Figure 11:
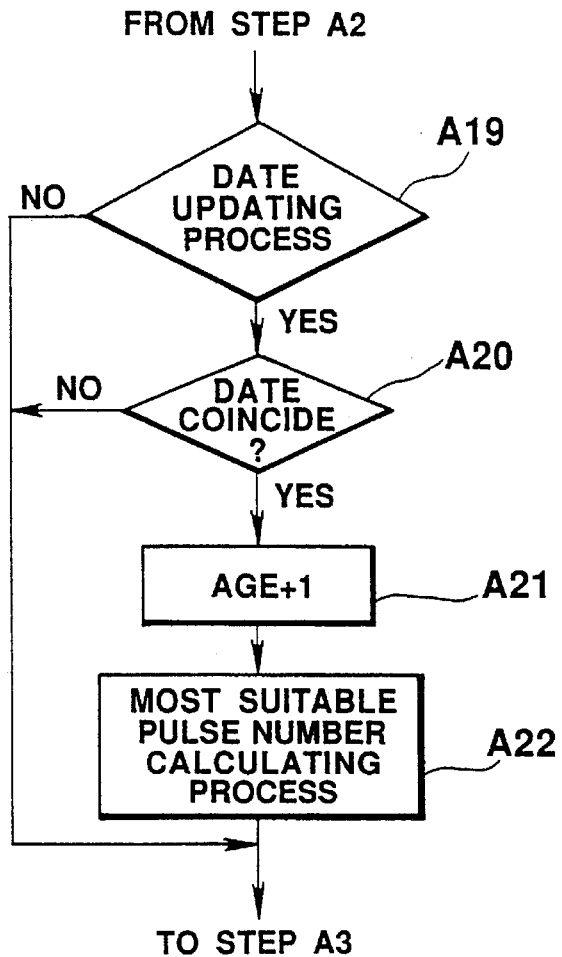
FIG. 11 is a flow chart of operation of the second embodiment.

When the process at step A2 of FIG. 4 has been finished, the control unit 7 goes to step A19 of FIG. 11. At step A19, it is judged whether the current time data stored in the time counting register 9b in the time counting process is updated. When "YES" at step A19, the control unit goes to step A20 while, when "NO" at step A19, then the control unit 7 goes to step A3 of FIG. 4.

When the current date data is updated, the control unit 7 advances from step A19 to step A20. At step A20, it is judged whether the current date data stored in the time counting register 9b coincides with the birthday data stored in the birthday memory 9j. When "YES" at step A20, the control unit goes to step A21 while, when "NO" at step A19, then the control unit 7 goes to step A3 of FIG. 4.

When it is judged at step A20 whether the current date data coincides with the birthday data, the control unit 7 advances from step A20 to step A21. At step A21, age data of the user stored in the age register 9c is added with +1, thereby being updated. At the following step A22, the most suitable pulse-number is calculated in a similar manner to step A15 of FIG. 4. More specifically, in the most suitable pulse-number calculating process, a pulse number corresponding to 60% of the maximum pulse number (220–age) for the user of the age is calculated and further a pulse number corresponding to 80% of the maximum pulse number (220–age) is calculated, using the age data updated at step A21. The pulse number corresponding to 60% of the maximum pulse number is stored in the pulse (1) register 9ee and the pulse number corresponding to 80% of the maximum pulse number is stored in the pulse (2) register 9f. After the process at step A22 has been finished, the control unit 7 goes to step A3 of FIG. 4.

As described above, since age data of the user stored in the RAM 9 is automatically updated in the second embodiment, the age updating process at step A14 of FIG. 4 can be omitted.

Third Embodiment

The third embodiment of the present invention will be described with reference to FIG. 12. A RAM 9 of the third embodiment similar to the RAM 9 of the second embodiment has a birthday memory 9j in addition to the registers of the RAM 9 of the first embodiment. The third embodiment is arranged such that age data is not previously stored in the age register 9c, but the age data is previously calculated every time the exercise level of difficulty calculation and the most suitable pulse-number calculation are performed.

Figure 12:
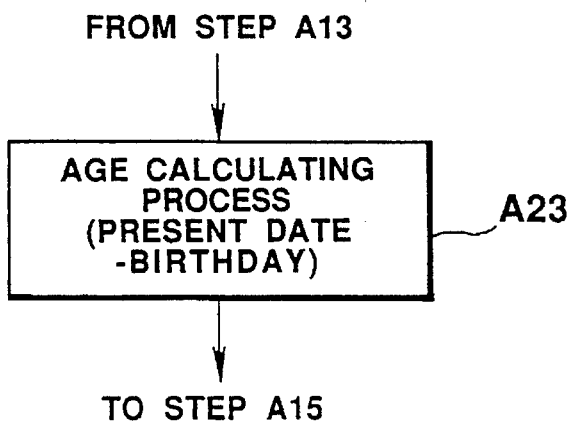
FIG. 12 is a flow chart of operation of a third embodiment of the present invention.

In the third embodiment, a step shown in FIG. 12 is added to the flowchart of FIG. 4. That is, the step A23 of FIG. 12 is performed in place of the age updating process at step A14 of FIG. 4.

Now, an operation of the third embodiment will be described in detail.

In the age setting mode (M=1), when the key S2 is manipulated, the control unit 7 advances from step A12 of FIG. 4 to step A13. The control unit 7 judges at step A13 that "M=1" is true, and goes to step A23 of FIG. 12. At step A23 of FIG. 12, age data of the user is calculated from current date data stored in the time counting register 9b and birthday data stored in the birthday memory 9j. The calculated age data is stored in the age register 9c of the RAM 9. After step A23, the control unit goes to step A15 of FIG. 4, where it calculates the most suitable pulse number from the age data, as described above.

In the third embodiment, the process at step A23 is added to the flowchart of FIG. 4 between step A6 and step A7. Therefore, when "YES" at step A6, the process at step A23 is executed, thereby age data being calculated. Then, the control unit 7 goes to step A7, where exercise level of difficulty data is calculated from the calculated age data.

Fourth Embodiment

The fourth embodiment of the present invention will be described with reference to FIGS. 13–16.

The fourth embodiment detects an electrocardiogram R-wave of the user to measure the number of his (or her) pulses, with use of electrodes which are mounted on a shirt of the user.

Figure 13:
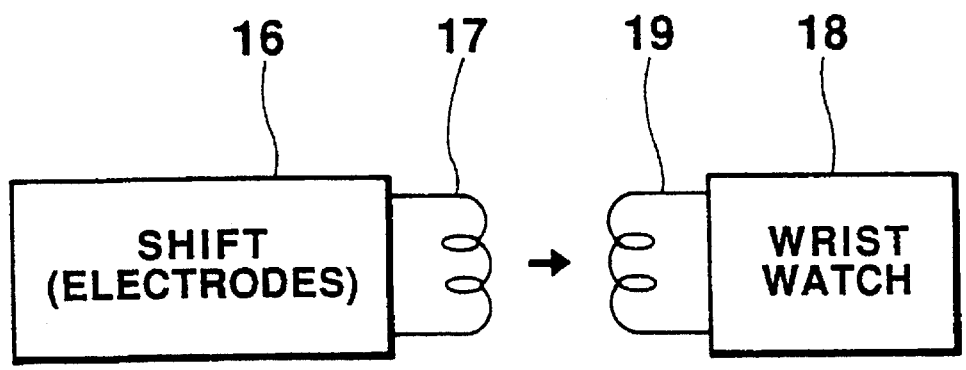
FIG. 13 is a block diagram showing a structure of an exercise level of difficulty display system of a fourth embodiment of the present invention.

FIG. 13 is a block diagram showing a structure of an exercise level of difficulty display system in the fourth embodiment.

The shirt 16 of the user is provided with an electronic circuit (to be described later) including a pair of electrodes for detecting an electrocardiogram R-wave and with a coil 17 for transmitting an electromagnetic inductive signal of the detected electrocardiogram R-wave.

A wrist watch 18 is put on the arm of the user who wears the shirt 16. The wrist watch 18 is provided with a coil 19 for receiving from the coil 17 the electromagnetic inductive signal of the detected electrocardiogram R-wave.

Figure 14:
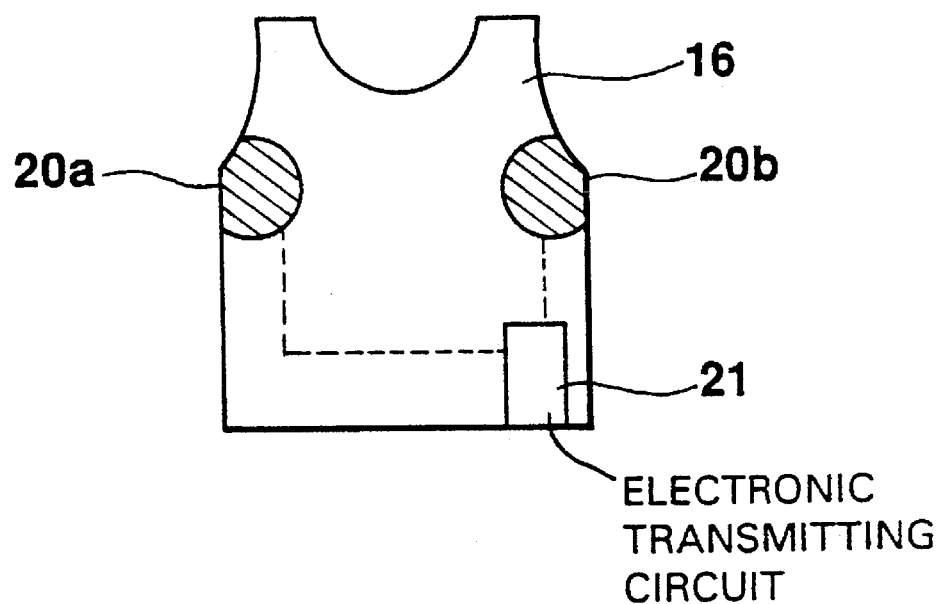
FIG. 14 is a view showing a structure of a shirt 16 of the fourth embodiment.

FIG. 14 is a view showing a structure of the shirt 16.

The shirt 16 is, for example, of a running-shirt shape, on both side portions of which a pair of electrodes 20a, 20b are mounted, as shown in FIG. 14. The electrodes 20a, 20b are kept in contact with a body of the user who wears the shirt 16. The electrodes 20a, 20b detect the electrocardiogram R-wave generated by the heart of the user, and transmit the detected electrocardiogram R-wave to the electronic circuit 21. The electronic circuit 21 is mounted on a west portion of the shirt 16. The electronic circuit 21 externally transmits through the coil 17 the electromagnetic inductive signal of the received electrocardiogram R-wave.

Figure 15:
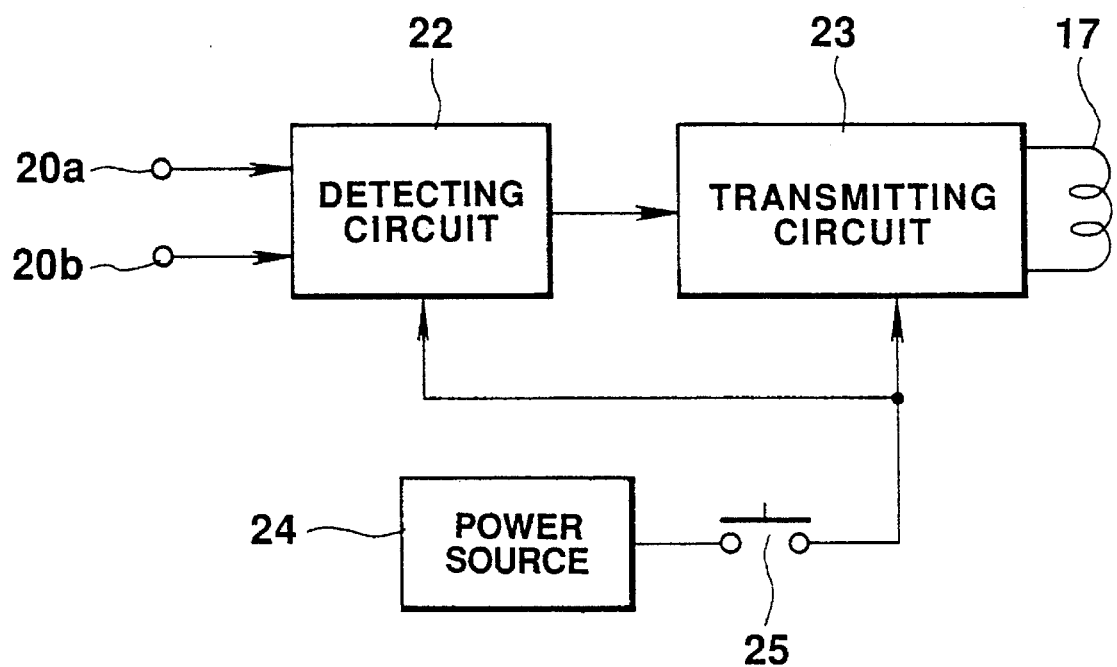
FIG. 15 is a circuit diagram of an electronic circuit 21 of the fourth embodiment.

FIG. 15 is a block diagram showing the electronic circuit 21 mounted on the shirt 16.

Figure 16:
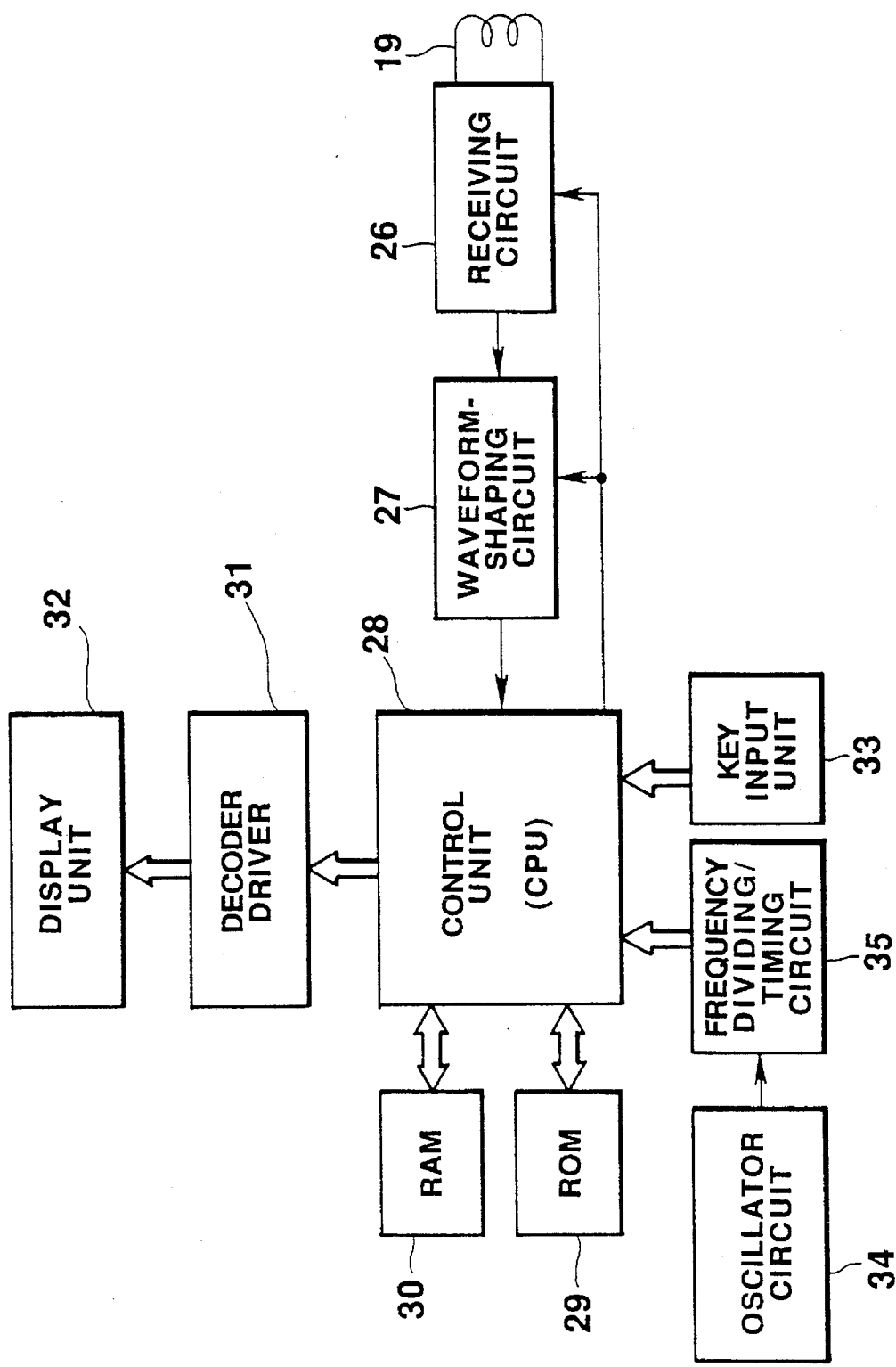
FIG. 16 is a circuit diagram of a wrist watch 18 of the fourth embodiment.

The pair of electrodes 20a, 20b for detecting an electrocardiogram R-wave are connected to a detecting circuit 22 to transmit the detected electrocardiogram R-wave thereto. The detecting circuit 22 amplifies the received electrocardiogram R-wave and supplies it to a transmitting circuit 23. The transmitting circuit 23 converts the electrocardiogram R-wave received from the detecting circuit 22 into an electromagnetic inductive signal, and sends it to the coil 17. The electromagnetic inductive signal sent from the coil 17 can be well detected at a distance of approximately 2 meters from the coil 17. A power circuit 24 includes, for example, a battery, and supplies a driving voltage through a power switch 25 to the detecting circuit 22 and the transmitting circuit FIG. 16 is a block diagram of a circuitry mounted in the wrist watch 18.

The coil 19, which is connected to a receiving circuit 26, receives the electromagnetic inductive signal of the electrocardiogram R-wave transmitted from the coil 17. The receiving circuit 26 receives the electrocardiogram R-wave from the coil 19, and transmits the same to a waveform-shaping circuit 27. The waveform-shaping circuit 27 shapes the waveform of the electrocardiogram R-wave transmitted from the receiving circuit 26, and supplies the electrocardiogram R-wave to a control unit 28. The receiving circuit 26 and the waveform-shaping circuit 27 start operations in response to an operation signal supplied from the control unit 28.

The control unit 28 is a central processing unit, which controls operations of peripheral units in accordance with a micro-program previously memorized in a ROM 29. The RAM 30 is a memory for storing various data. A decoder driving circuit 31 outputs to a display unit 32 a display driving signal based on display data output from the control unit 28, thereby driving the display unit 32. The display unit 32, having liquid crystal display elements, displays a present time, the number of pulses and the like.

A key input unit 33 is provided with the keys S1 to S3, and outputs a key input signal responsive to a key input operation to the control unit 28. An oscillator circuit 34 generates a clock signal of a predetermined frequency, and outputs the clock signal to a frequency dividing/timing circuit 35. The frequency dividing/timing circuit 35 divides the clock signal sent from the oscillator circuit 34 to generate various timing signals such as a time counting signal. The timing signals are supplied to the control unit 28.

The operation of the fourth embodiment is the same as the first embodiment as illustrated in FIGS. 3–9, with exception of the pulse detecting process, and the description thereof is omitted. In the fourth embodiment, the electrocardiogram R-wave is transmitted and received electromagnetic inductively, but the transmission of an electromagnetic wave of the electrocardiogram R-wave may be executed with use of a transmitting device and an antenna.

Fifth Embodiment

The fifth embodiment of the present invention will be described with reference to FIGS. 17 and 18.

The fifth embodiment is arranged such that the user can arbitrarily set a pulse number at the most suitable exercise level of difficulty depending on his physical condition.

The user can use the apparatus of the fifth embodiment in various ways. For example, when the user takes some exercise after he recovers his health, he can set a suitable pulse number for the most suitable exercise level of difficulty to low levels such as 55% to 65% of the maximum pulse number, and gradually raises the exercise load to recover his physical strength in an appropriate manner. For the user who has well trained, the pulse number can be set to high levels (a training zone): 80% to 90% of the maximum pulse number for the most suitable exercise level of difficulty to Greatly develop his physical strength.

Figure 17:
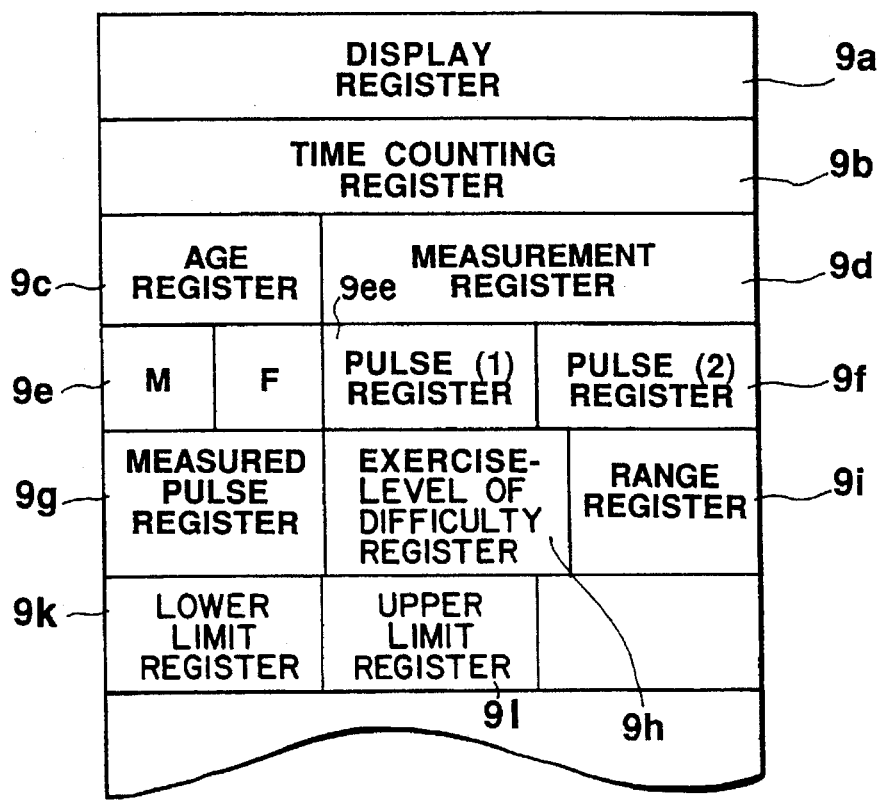
FIG. 17 is a view showing a memory structure of RAM 9 of a fifth embodiment of the present invention.

FIG. 17 is a view showing a memory structure of the RAM 9 of the fifth embodiment. The memory structure of the RAM 9 in the fifth embodiment has a similar structure to the RAM 9 of the first embodiment, but is further provided with an upper limit register 9l and a lower limit register 9k. The upper limit register 9l is for storing an upper limit percentage value of the exercise level of difficulty. The lower limit register 9k is for storing a lower limit percentage value of the exercise level of difficulty. To set these percentage values in the registers 9l, 9k, the key S3 is manipulated to set a range setting mode. Then, the upper limit percentage value can be set to the upper limit register 9l, by manipulating the key S1 while the lower limit percentage value can be set to the lower limit register 9k by manipulating the key S2.

Now, the operation of the fifth embodiment of the invention will be described.

Figure 18:
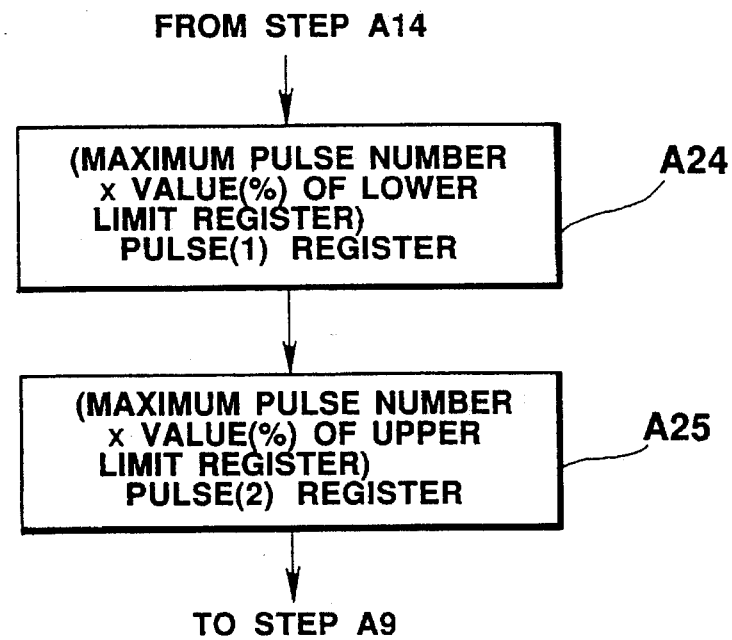
FIG. 18 is a flow chart of operation of the fifth embodiment.

In the fifth embodiment, step A24 and A25 shown in FIG. 18 are added to the flowchart of FIG. 4 in place of the step A15. In other words, when the age updating process at step A14 of FIG. 4 has been finished, the control unit 28 goes to step A24 of FIG. 18. At step 24, an arithmetic operation: (the maximum pulse number for the age of the user)×(a value (%) of the lower limit register 9k). The resultant product (the lower limit of the most suitable pulse number) is stored in the pulse (1) register 9ee. At the following step 25, an arithmetic operation is performed: (the maximum pulse number for the age of the user)×(a value (%) of the upper limit register 9l). The resultant product (the upper limit of the most suitable pulse number) is stored in the pulse (2) register 9f.

After step A25, the control unit 28 goes to step A9 of FIG. 4. In this manner, the most suitable pulse number is calculated based on the upper limit percentage value and the lower limit percentage value, which have been arbitrarily set by the user.

In the first to the fourth embodiments, the most suitable pulse-number range for the most suitable exercise level of difficulty is set to 60% to 80% of the maximum pulse number, but the range is not always limited to these values. A pulse number corresponding to 75% of the maximum pulse number may be calculated and displayed as a target pulse number. The maximum pulse number is calculated from the expression: "220–AGE", but the maximum pulse numbers for respective ages of users may be previously memorized in a memory such as a ROM and are read out therefrom every time an arithmetic operation is performed. Pulses are detected and measured by methods other than in the above embodiments. For example, sounds and pressure may be used to detect or measure pulses.

In the above embodiments, the pulse measuring process is effected while the user is taking exercise, but the pulse measuring process may be effected when the time counting process is stopped. Further, in the embodiments, the apparatus according to the present invention is applied to the electronic wrist watch, but the apparatus may be applied to other electronic appliances, for example, a training instrument such as an ergometer and an instrument specialized for measuring pulses, which will be prepared for exerciser convenience at a training center.

In the above embodiments, the obtained exercise level of difficulty data is displayed on the liquid crystal display unit of the electronic wrist watch. The obtained exercise level of difficulty data, however, may be transmitted to a separate appliance, or may be printed by a printing device mounted on the apparatus body or by a separate printer.

Several embodiments of the present invention have been described in detail but these embodiments are simply illustrative and not restrictive. The present invention may be modified in various manners. All the modifications and applications of the present invention will be within the scope and spirit of the invention, so that the scope of the present invention should be determined only by what is recited in the present appended claims and their equivalents.

What is claimed is:

1. Apparatus to automatically monitor exercise level of difficulty, comprising:

age-data output means for providing age data of a user;

pulse-rate determining means for converting pulse signals of said user to a pulse rate to obtain pulse number data;

means for deriving exercise level of difficulty data from the pulse-number data obtained by said pulse-rate determining means and the age data output by said age-data output means; and output means for outputting the exercise level of difficulty data derived by said means for deriving exercise level of difficulty data.

2. The exercise level of difficulty monitoring apparatus according to claim 1, wherein said exercise level of difficulty deriving means provides exercise level of difficulty data expressed in terms of a ratio to a maximum exercise level of difficulty data for every age data.

3. The exercise level of difficulty monitoring apparatus according to claim 1, wherein said output means includes display means for visually displaying the exercise level of difficulty data, said display means being provided with display members which indicate that the exercise level of difficulty data falls within a predetermined range.

4. The exercise level of difficulty monitoring apparatus according to claim 1, wherein said age-data output means comprises:

age-data storing means for storing age data;

date counting means for counting reference signals to obtain at least date data of that day; and age updating means for updating the age data stored in said age-data storing means when the date data obtained by said date counting means reaches predetermined date data, and for outputting updated age data.

5. The exercise level of difficulty monitoring apparatus according to claim 1, wherein said age-data output means comprises:

birthday-data storing means for storing birthday data;

date counting means for counting reference signals to obtain at least date data of that day; and age calculating means for calculating age data from the date data obtained by said date counting means and the birthday data stored in said birthday-data storing means, and for outputting the calculated age data.

6. Apparatus for automatically monitoring exercise level of difficulty, comprising:

age-data output means for providing age data of a user;

means for obtaining first pulse-number data which define a predetermined range of most suitable exercise level of difficulty for an age of the user, based on the age data provided by said age-data output means;

first pulse-number data output means for outputting the first pulse-number data;

pulse-rate determining means for converting pulse signals of said user to a pulse rate to obtain second pulse-number data; and second pulse-number data output means for outputting the second pulse-number data obtained by said pulse-rate determining means.

7. The exercise level of difficulty monitoring apparatus according to claim 6, wherein the first pulse-number data define a pulse-number range which has at a center thereof a pulse number for exercise level of difficulty of 75% of maximum exercise level of difficulty for the age data output by said age-data output means.

8. The exercise level of difficulty monitoring apparatus according to claim 6, wherein at least one of said first pulse-number data output means and said second pulse-number data output means includes display means for visually displaying the respective first and second pulse-number data, said display means being provided with range indicating means for indicating whether the pulse-number data obtained by said pulse-rate determining means falls within the predetermined range.

9. The exercise level of difficulty monitoring apparatus according to claim 6, wherein said age-data output means comprises:

age-data storing means for storing age data of the user;

date counting means for counting reference signals to obtain at least date data of that day; and age updating means for updating the age data stored in said age-data storing means when the date data obtained by said date counting means reaches predetermined date data, and for outputting updated age data.

10. The exercise level of difficulty monitoring apparatus according to claim 6, wherein said age-data output means comprises:

birthday-data storing means for storing birthday data;

date counting means for counting reference signals to obtain at least date data of that day; and age calculating means for calculating age data from the date data obtained by said date counting means and the birthday data stored in said birthday-data storing means, and for outputting calculated age data.

11. A data display apparatus comprising:

age-data output means providing age data of a user;

pulse-number data calculating means for calculating first pulse-number data corresponding to predetermined exercise level of difficulty for each age of a user, based on the age data provided by said age-data output means;

pulse-number data display means for displaying the first pulse-number data;

pulse-number data output means for providing second pulse-number data;

means for deriving exercise level of difficulty data, based on the second pulse-number data output by said pulse-number data output means and the age data output by said age-data output means; and exercise level of difficulty data display means for displaying the exercise level of difficulty data.

12. The data display apparatus according to claim 11, wherein said pulse-number data display means is provided with means which displays, with use of a plurality of display members, the pulse number data calculated by said pulse-number data calculating means.

13. The data display apparatus according to claim 11, wherein said pulse-number data display means comprises:

a plurality of first display members; and first display control means for driving a particular first display member from among the plurality of first display members which corresponds to the first pulse-number data; and said exercise level of difficulty data display means comprises:

a plurality of second display members; and second display control means for driving a particular second display member from among the plurality of second display members which corresponds to the exercise level of difficulty data.

14. Apparatus for automatically monitoring exercise level of difficulty, comprising:

age-data output means for outputting age data of a user;

exercise level of difficulty setting means for setting ratio data in terms of a ratio of desired exercise level of difficulty to maximum exercise level of difficulty;

ratio-data storing means for storing the ratio data set by said exercise level of difficulty setting means;

means for deriving a ratio of a maximum pulse number for the age data output by said age-data output means to obtain first pulse-number data, said ratio being expressed by said ratio data;

first pulse-number output means for outputting the first pulse-number data obtained by said pulse-number calculating means;

pulse-rate determining means for converting pulse signals of the user to a pulse rate to obtain second pulse-number data; and second pulse-number output means for outputting the second pulse-number data obtained by said pulse-number counting means.

15. The exercise level of difficulty monitoring apparatus according to claim 14, wherein said exercise level of difficulty setting means sets a plurality of different ratio data.

16. The exercise level of difficulty monitoring apparatus according to claim 14, wherein at least one of said first pulse-number output means and said second pulse number output means includes a display means for displaying the first or second pulse-number data, said display means being provided with range indicating means for indicating whether pulse-number data obtained by pulse-number measuring means falls within a range of the first pulse-number data obtained by said pulse-number calculating means.

* * * * *